US011617625B2

(12) United States Patent
Rosinski

(10) Patent No.: US 11,617,625 B2
(45) Date of Patent: Apr. 4, 2023

(54) SYSTEMS, APPARATUS AND METHODS FOR PROPERLY LOCATING ITEMS

(71) Applicant: Medline Industries, LP, Northfield, IL (US)

(72) Inventor: Jared Rosinski, Gurnee, IL (US)

(73) Assignee: Medline Industries, LP, Northfield, IL (US)

(*) Notice: Subject to any disclaimer, the term of this patent is extended or adjusted under 35 U.S.C. 154(b) by 548 days.

(21) Appl. No.: 16/815,925

(22) Filed: Mar. 11, 2020

(65) Prior Publication Data

US 2020/0289206 A1 Sep. 17, 2020

Related U.S. Application Data

(60) Provisional application No. 62/817,151, filed on Mar. 12, 2019.

(51) Int. Cl.
*A61B 34/20* (2016.01)
*A61B 34/00* (2016.01)
(Continued)

(52) U.S. Cl.
CPC .............. *A61B 34/20* (2016.02); *A61B 5/742* (2013.01); *A61B 5/7405* (2013.01);
(Continued)

(58) Field of Classification Search
CPC ........... A61B 2017/00115; A61B 2017/00119; A61B 2017/00221; A61B 2018/00303;
(Continued)

(56) References Cited

U.S. PATENT DOCUMENTS 2,698,270 A 12/1954 Mesek
3,097,649 A 7/1963 Gray
(Continued)

FOREIGN PATENT DOCUMENTS

DE 39178765 12/1990
EP 0948940 10/1999
(Continued)

OTHER PUBLICATIONS

Third Party Submission Under 37 CFR 1.290 for U.S. Appl. No. 16/994,157 dated Dec. 21, 2021.
(Continued)

*Primary Examiner* — George Manuel
(74) *Attorney, Agent, or Firm* — Fitch, Even, Tabin & Flannery LLP

(57) ABSTRACT

Systems, methods and apparatus are disclosed for properly using and locating object retention wands via the use of at least one sensor located on or in the wand body for determining when the wand is capable of properly scanning a target area. In one form, a proximity sensor is used. In another form a motion sensor is used. In still other forms, both a proximity sensor and motion sensor are used. In some forms, the wand system further includes an indicator for indicating whether the wand is within proper read range, speed and/or orientation of a target area so as to confirm proper use of the wand to locate retained objects before concluding a procedure. In other forms one or more of a user interface, scanner and network interface may also be used with the system. Further systems, methods and apparatus are also disclosed herein.

30 Claims, 5 Drawing Sheets

(51) Int. Cl.
   *A61B 90/30* (2016.01)
   *A61B 5/00* (2006.01)
(52) U.S. Cl.
   CPC ............ *A61B 5/7465* (2013.01); *A61B 34/25* (2016.02); *A61B 34/76* (2016.02); *A61B 34/77* (2016.02); *A61B 90/30* (2016.02); *A61B 2560/0271* (2013.01); *A61B 2560/0437* (2013.01); *A61B 2560/0487* (2013.01); *A61B 2562/0219* (2013.01); *A61B 2562/0257* (2013.01)
(58) Field of Classification Search
   CPC .... A61B 2034/2048; A61B 2034/2065; A61B 2090/0805; A61B 2090/0807; A61B 2090/371; A61B 2560/0271; A61B 2560/0437; A61B 2560/0487; A61B 2562/0219; A61B 2562/0257; A61B 34/20; A61B 34/25; A61B 34/76; A61B 34/77; A61B 5/7405; A61B 5/742; A61B 5/7465; A61B 90/30; A61B 90/36; A61B 90/96; A61B 90/98
   See application file for complete search history.

(56) References Cited

U.S. PATENT DOCUMENTS

| | | | |
|---|---|---|---|
| 3,367,431 | A | 2/1968 | Prindle |
| 3,422,816 | A | 1/1969 | Robinson |
| 3,464,415 | A | 9/1969 | Brownlee |
| 3,587,583 | A | 6/1971 | Greenberg |
| 3,698,393 | A | 10/1972 | Stone |
| 3,834,390 | A | 9/1974 | Hirsch |
| 3,853,117 | A | 12/1974 | Murr |
| 3,941,132 | A | 3/1976 | Lenaghan |
| 3,965,907 | A | 6/1976 | Hardy |
| 4,075,632 | A | 2/1978 | Baldwin |
| 4,098,728 | A | 7/1978 | Rosenblatt |
| 4,114,601 | A | 9/1978 | Abels |
| 4,193,405 | A | 3/1980 | Abels |
| 4,205,680 | A | 6/1980 | Marshall |
| 4,244,369 | A | 1/1981 | McAvinn |
| 4,264,575 | A | 4/1981 | Zimmerman |
| 4,422,548 | A | 12/1983 | Cheesman |
| 4,477,256 | A | 10/1984 | Hirsch |
| 4,626,251 | A | 12/1986 | Shen |
| 4,639,253 | A | 1/1987 | Dyer |
| 4,645,499 | A | 2/1987 | Rupinskas |
| 4,658,818 | A | 4/1987 | Miller, Jr. |
| 4,711,996 | A | 12/1987 | Drexler |
| 4,718,897 | A | 1/1988 | Elves |
| 4,739,328 | A | 4/1988 | Koelle |
| 4,832,198 | A | 5/1989 | Alikhan |
| 4,917,694 | A | 4/1990 | Jessup |
| 4,943,939 | A | 7/1990 | Hoover |
| 5,031,642 | A | 7/1991 | Nosek |
| 5,041,103 | A | 8/1991 | Rupinskas |
| 5,045,080 | A | 9/1991 | Dyer |
| 5,049,219 | A | 9/1991 | Johns |
| 5,057,095 | A | 10/1991 | Fabian |
| 5,074,840 | A | 12/1991 | Yoon |
| 5,099,845 | A | 3/1992 | Besz |
| 5,105,829 | A | 4/1992 | Fabian |
| 5,107,862 | A | 4/1992 | Fabian |
| 5,112,325 | A | 5/1992 | Zachry |
| 5,188,126 | A | 2/1993 | Fabian |
| 5,211,129 | A | 5/1993 | Taylor |
| 5,231,273 | A | 7/1993 | Caswell |
| 5,300,922 | A | 4/1994 | Stoffer |
| 5,329,944 | A | 7/1994 | Fabian |
| 5,374,813 | A | 12/1994 | Shipp |
| 5,443,082 | A | 8/1995 | Mewburn |
| 5,456,718 | A | 10/1995 | Szymaitis |
| 5,463,376 | A | 10/1995 | Stoffer |
| 5,541,604 | A | 7/1996 | Meier |
| 5,610,811 | A | 3/1997 | Honda |
| 5,629,498 | A | 5/1997 | Pollock |
| 5,637,850 | A | 6/1997 | Honda |
| 5,650,596 | A | 7/1997 | Morris |
| 5,664,582 | A | 9/1997 | Szymaitis |
| 5,678,569 | A | 10/1997 | Chew |
| 5,681,862 | A | 10/1997 | Hollis |
| 5,805,451 | A | 9/1998 | Speas |
| 5,833,603 | A | 11/1998 | Kovacs |
| 5,923,001 | A | 7/1999 | Morris |
| 5,931,824 | A | 8/1999 | Stewart |
| 5,944,023 | A | 8/1999 | Johnson |
| 5,991,728 | A | 11/1999 | Debusk |
| 6,009,878 | A | 1/2000 | Weijand |
| 6,026,818 | A | 2/2000 | Blair |
| 6,076,007 | A | 6/2000 | England |
| 6,223,137 | B1 | 4/2001 | McCay |
| 6,272,368 | B1 | 8/2001 | Alexandrescu |
| 6,305,381 | B1 | 10/2001 | Weijand |
| 6,366,206 | B1 | 4/2002 | Ishikawa |
| 6,777,623 | B2 | 8/2004 | Ballard |
| 6,861,954 | B2 | 3/2005 | Levin |
| 6,998,541 | B2 | 2/2006 | Morris |
| 7,019,650 | B2 | 3/2006 | Volpi |
| 7,118,029 | B2 | 3/2006 | Nycz |
| 7,135,978 | B2 | 11/2006 | Gisselberg |
| 7,158,030 | B2 | 1/2007 | Chung |
| 7,158,754 | B2 | 1/2007 | Anderson |
| 7,180,014 | B2 | 2/2007 | Farber |
| 7,256,696 | B2 | 8/2007 | Levin |
| 7,268,684 | B2 | 9/2007 | Tethrake |
| 7,297,834 | B1 | 11/2007 | Shapiro |
| D557,421 | S | 12/2007 | Fleck |
| 7,307,530 | B2 | 12/2007 | Fabian |
| 7,411,506 | B2 | 1/2008 | Volpi |
| 7,399,899 | B2 | 7/2008 | Fabian |
| 7,420,468 | B2 | 9/2008 | Fabian |
| 7,464,713 | B2 | 12/2008 | Fabian |
| 7,518,502 | B2 | 4/2009 | Austin |
| 7,530,967 | B2 | 5/2009 | Brown |
| 7,541,933 | B2 | 6/2009 | Volpi |
| 7,557,710 | B2 | 7/2009 | Sanchez |
| 7,557,711 | B2 † | 7/2009 | Volpi |
| 7,589,634 | B2 | 9/2009 | Frank |
| 7,696,877 | B2 | 4/2010 | Barnes |
| 7,703,674 | B2 | 4/2010 | Stewart |
| 7,774,244 | B2 | 8/2010 | Kreiner |
| 7,787,931 | B2 | 8/2010 | Fabian |
| 7,795,491 | B2 | 9/2010 | Stewart |
| D631,152 | S | 1/2011 | Hampton |
| 7,893,840 | B2 | 2/2011 | Volpi |
| D634,004 | S | 3/2011 | Hampton |
| D636,871 | S | 4/2011 | Hampton |
| 8,063,760 | B2 | 11/2011 | Volpi |
| 8,105,296 | B2 | 1/2012 | Morris |
| 8,181,860 | B2 | 5/2012 | Fleck |
| 8,193,938 | B2 | 6/2012 | Halberthal |
| 8,279,068 | B2 | 10/2012 | Morris |
| 8,479,989 | B2 | 1/2013 | Fleck |
| 8,576,076 | B2 | 1/2013 | Morris |
| 8,428,517 | B2 | 4/2013 | Ting |
| 8,544,660 | B2 | 10/2013 | Foley |
| 8,554,579 | B2 | 10/2013 | Tribble |
| 8,710,957 | B2 † | 4/2014 | Blair |
| 8,792,693 | B2 | 7/2014 | Satish |
| 8,872,662 | B2 | 10/2014 | Halberthal |
| 8,897,523 | B2 | 11/2014 | Satish |
| 8,978,229 | B2 | 3/2015 | Halberthal |
| 8,983,167 | B2 | 3/2015 | Satish |
| 8,985,446 | B2 | 3/2015 | Fleck |
| 9,019,078 | B2 | 4/2015 | Hamelin |
| 9,035,748 | B2 | 5/2015 | Greefkes |
| 9,047,663 | B2 | 6/2015 | Satish |
| 9,070,270 | B2 | 6/2015 | Kreiner |
| 9,168,104 | B2 | 10/2015 | Dein |
| 9,171,368 | B2 | 10/2015 | Satish |
| 9,198,727 | B1 | 12/2015 | Samuels |
| 9,289,943 | B2 | 3/2016 | Halberthal |

(56) References Cited

U.S. PATENT DOCUMENTS

| | | |
|---|---|---|
| 9,471,820 B2 | 10/2016 | Arthaber |
| 9,474,693 B2 | 10/2016 | Ranalletta |
| 9,507,981 B2 | 11/2016 | Dor |
| 9,662,273 B2 | 2/2017 | Ranalletta |
| 9,595,104 B2 | 3/2017 | Satish |
| 9,646,375 B2 | 5/2017 | Satish |
| 9,652,655 B2 | 5/2017 | Satish |
| 9,773,320 B2 | 9/2017 | Satish |
| 9,824,441 B2 | 11/2017 | Satish |
| 9,870,625 B2 | 1/2018 | Satish |
| 9,936,906 B2 | 4/2018 | Satish |
| 10,002,269 B2 † | 6/2018 | Dor |
| 10,154,885 B1 | 12/2018 | Barnett |
| 10,282,839 B2 | 5/2019 | Satish |
| 10,424,060 B2 | 9/2019 | Satish |
| 10,426,356 B2 | 10/2019 | Satish |
| 10,528,782 B2 | 1/2020 | Satish |
| 10,555,675 B2 | 2/2020 | Satish |
| 10,641,644 B2 | 5/2020 | Satish |
| 10,706,541 B2 | 7/2020 | Satish |
| 10,719,747 B2 | 7/2020 | Stewart |
| 10,789,710 B2 | 9/2020 | Satish |
| 10,863,933 B2 | 12/2020 | Satish |
| 10,905,521 B2 | 2/2021 | Stewart |
| 10,957,179 B2 | 3/2021 | Satish |
| 11,009,600 B2 | 5/2021 | Kambiz |
| 11,109,941 B2 | 9/2021 | Kumar |
| 2002/0049650 A1 | 4/2002 | Reff |
| 2002/0090930 A1 | 7/2002 | Fujiwara |
| 2003/0105394 A1 | 6/2003 | Fabian |
| 2003/0224996 A1 | 12/2003 | Opperman |
| 2004/0077546 A1 | 4/2004 | Oppermann |
| 2004/0169587 A1 | 9/2004 | Washington |
| 2005/0038556 A1 | 2/2005 | Gagnon |
| 2005/0075564 A1 | 4/2005 | Ballard |
| 2005/0255141 A1 | 11/2005 | Oppermann |
| 2006/0029591 A1 | 2/2006 | Vukicevic |
| 2006/0044137 A1 | 3/2006 | Morris |
| 2006/0065739 A1 | 3/2006 | Falls |
| 2006/0140464 A1 | 6/2006 | Feilkas |
| 2006/0241396 A1 | 10/2006 | Fabian |
| 2006/0241399 A1 | 10/2006 | Fabian |
| 2006/0256081 A1 | 11/2006 | Zalewski |
| 2006/0264260 A1 | 11/2006 | Zalewski |
| 2006/0282873 A1 | 12/2006 | Zalewski |
| 2006/0287086 A1 | 12/2006 | Zalewski |
| 2006/0287087 A1 | 12/2006 | Zalewski |
| 2007/0015558 A1 | 1/2007 | Zalewski |
| 2007/0015559 A1 | 1/2007 | Zalewski |
| 2007/0083170 A1 | 4/2007 | Stewart |
| 2007/0094303 A1 | 4/2007 | Zwingenberger |
| 2007/0103313 A1 | 5/2007 | Washington |
| 2007/0125392 A1 | 6/2007 | Olson |
| 2007/0166353 A1 | 7/2007 | Oppermann |
| 2007/0268133 A1 | 11/2007 | Sanchez |
| 2007/0285249 A1 | 12/2007 | Blair |
| 2008/0043901 A1 | 2/2008 | Maschke |
| 2008/0051746 A1 | 2/2008 | Shen-Gunther |
| 2008/0096654 A1 | 4/2008 | Mondesir |
| 2008/0098448 A1 | 4/2008 | Mondesir |
| 2008/0100825 A1 | 5/2008 | Zalewski |
| 2008/0138289 A1 | 6/2008 | Goronkin |
| 2008/0174409 A1 | 7/2008 | Frank |
| 2008/0204245 A1 | 8/2008 | Blair |
| 2008/0233170 A1 | 9/2008 | Oppermann |
| 2008/0237341 A1 | 10/2008 | Fleck |
| 2008/0269597 A1 | 10/2008 | Benetti |
| 2008/0272913 A1 | 11/2008 | Barnes |
| 2009/0014518 A1 | 1/2009 | Stewart |
| 2009/0317002 A1 | 12/2009 | Dein |
| 2010/0010372 A1 | 1/2010 | Brown |
| 2010/0074883 A9 | 3/2010 | Slobodan |
| 2010/0090901 A1 | 4/2010 | Smith |
| 2010/0132600 A1 | 6/2010 | Dean |
| 2010/0160865 A1 | 6/2010 | Zeltzer |
| 2010/0191107 A1* | 7/2010 | Bowers ............... A61B 6/5247 250/363.01 |
| 2010/0258632 A1 | 10/2010 | Good |
| 2010/0305714 A1 | 12/2010 | Procter |
| 2011/0174877 A1 | 7/2011 | Fleck |
| 2011/0306899 A1 | 12/2011 | Brown |
| 2012/0062365 A1 | 3/2012 | Hansen |
| 2012/0075464 A1 | 3/2012 | Derenne |
| 2012/0095422 A1 | 4/2012 | Morris |
| 2012/0132600 A1 | 5/2012 | Foley |
| 2012/0146789 A1 | 6/2012 | De Luca |
| 2013/0021192 A1 | 1/2013 | Daly |
| 2013/0037663 A1 | 2/2013 | Walther |
| 2013/0149294 A1 | 6/2013 | Rueger |
| 2013/0186413 A1 | 7/2013 | Haines |
| 2013/0301901 A1 | 11/2013 | Satish |
| 2014/0021087 A1 | 1/2014 | Adler |
| 2014/0055618 A1 | 2/2014 | Myers |
| 2014/0126788 A1 | 5/2014 | Satish |
| 2014/0128838 A1 | 5/2014 | Satish |
| 2014/0165740 A1 | 6/2014 | Speidel |
| 2014/0243770 A1 | 8/2014 | Stewart |
| 2014/0261457 A1 | 9/2014 | Lother |
| 2015/0109442 A1 | 4/2015 | Derenne |
| 2015/0164603 A1 | 6/2015 | Fleck |
| 2015/0193127 A1 | 7/2015 | Chai |
| 2015/0261291 A1 | 9/2015 | Mikhailov |
| 2015/0273102 A1 | 10/2015 | Hissink |
| 2015/0280649 A1 | 10/2015 | Nero, Jr. |
| 2015/0342745 A1 | 12/2015 | Roux |
| 2015/0363618 A1 | 12/2015 | Fleck |
| 2016/0008091 A1 | 1/2016 | Saotome |
| 2016/0045279 A1 | 2/2016 | Daon |
| 2016/0051418 A1 | 2/2016 | Fleck |
| 2016/0065909 A1 | 3/2016 | Derenne |
| 2016/0070942 A1 | 3/2016 | Dor |
| 2016/0085922 A1 | 3/2016 | Sweeney |
| 2016/0171262 A1 | 6/2016 | Fleck |
| 2016/0212577 A1 | 7/2016 | Dor |
| 2016/0379504 A1 | 12/2016 | Bailey |
| 2017/0143429 A1 | 5/2017 | Richmond |
| 2017/0151386 A1 | 6/2017 | Walther |
| 2017/0184442 A1 | 6/2017 | Satish |
| 2017/0224437 A1 | 8/2017 | Fleck |
| 2017/0258547 A1 | 9/2017 | Karasina |
| 2017/0296301 A1 | 10/2017 | Dor |
| 2018/0068179 A1 | 3/2018 | Derenne |
| 2018/0204103 A1 | 7/2018 | Dor |
| 2018/0227547 A1 | 8/2018 | Derenne |
| 2018/0243044 A1 | 8/2018 | Fleck |
| 2018/0285704 A1 | 10/2018 | Stewart |
| 2018/0338801 A1 | 11/2018 | Barnett |
| 2018/0344429 A1 | 12/2018 | Stewart |
| 2018/0353256 A1 | 12/2018 | Stewart |
| 2019/0000589 A1 | 1/2019 | Vanderwoude |
| 2019/0235069 A1 | 8/2019 | Shaorinejad |
| 2019/0244707 A1 | 8/2019 | Becker |
| 2019/0349554 A1 | 11/2019 | Derenne |
| 2020/0143190 A1 | 5/2020 | Hastings |
| 2020/0315732 A1 | 10/2020 | Fleck |
| 2020/0320359 A1 | 10/2020 | Stewart |
| 2021/0019672 A1 | 1/2021 | Paramasivan |
| 2021/0085428 A1 | 3/2021 | Yavari |
| 2021/0128270 A1 | 5/2021 | Stewart |
| 2021/0259800 A1 | 8/2021 | Fleck |

FOREIGN PATENT DOCUMENTS

| | | |
|---|---|---|
| EP | 1219259 | 7/2002 |
| EP | 1610704 A1 | 1/2006 |
| WO | 9422580 | 10/1994 |
| WO | 199527252 | 10/1995 |
| WO | 199745057 | 12/1997 |
| WO | 9830166 | 7/1998 |
| WO | 2004086997 | 10/2004 |
| WO | 2014165740 | 10/2014 |
| WO | 2015017044 | 2/2015 |

(56) References Cited

FOREIGN PATENT DOCUMENTS

| WO | 2016176187 | 11/2016 |
|---|---|---|
| WO | 2017112051 | 6/2017 |
| WO | 2018217396 | 11/2018 |

OTHER PUBLICATIONS

Patent Cooperation Treaty, International Searching Authority, Notification of Transmittal of the International Search Report and the Written Opinion of the International Searching Authority, or the Declaration, issued in International Application No. PCT/US2020/022380 dated Jul. 7, 2020, 169 pp.
Clearcount Medical Solutions, Inc., "The SmartSponge System Operating Procedures Manual", Jan. 31, 2006, 54 pp.
Haldor Advanced Technologies Ltd., 510(k) Summary (21 CFR 807.92) ORLocateTM System, Aug. 12, 2010, 7 pp.
Haldor Advanced Technologies, ORLocate Sponge Solution Product Information Sheet, 2017, 2 pp.
Patent Cooperation Treaty, International Searching Authority, Notification of Transmittal of the International Search Report and the Written Opinion of the International Searching Authority, or the Declaration, issued in International Patent Application No. PCT/US2018/029556 dated Aug. 10, 2018; 17 pages.
U.S. Food & Drug Administration, 510(k) Premarket Notification, https://accessdata.fda.gov/scripts/cdrh/cfdocs/cfpmn.cfm?ID=K100551, Mar. 27, 2018, 3 pp.
Extended European Search Report from related European Patent Application No. 18805371.4 dated Feb. 18, 2021; 13 pages.

\* cited by examiner
† cited by third party

SYSTEMS, APPARATUS AND METHODS FOR PROPERLY LOCATING ITEMS

CROSS-REFERENCE TO RELATED APPLICATIONS

This application claims the benefit of U.S. Provisional Application No. 62/817,151, filed Mar. 12, 2019, and is hereby incorporated herein by reference in its entirety.

FIELD

This invention relates generally to systems, methods and apparatus for locating items/objects and, more particularly, to systems, methods and apparatus for properly locating items that are tagged with passive or active tracking devices to locate items misplaced such as in the laundry, biohazard or trash bins, or a procedural area/arena (including in a patient) prior to, during, near the conclusion, or after the conclusion of a procedure.

BACKGROUND

Medical procedures have evolved over time into very efficient and well-choreographed routines, often using pre-packaged surgical kits containing all instruments and equipment needed for the particular procedure at hand. However, these routines often involve numerous medical personnel working with a litany of different tools and pieces of equipment, often times in a relatively small or cramped space. This is true whether the procedure is being performed in a clinical setting or in a high-tech operating room. In such procedures and environments, one of the most difficult things to do is track all tools, equipment or items being used during the procedure to make sure all are accounted for at the end of the procedure and that none are left where they shouldn't be left.

Conventional systems exist to track various items throughout a medical procedure, but all have their own shortcomings. For example, smart sponge systems exist that track how many sponges have been used during a procedure, how many have been returned or discarded, and how many remain out and unaccounted for. Often these systems are blind systems that simply note when an item is unaccounted for and require medical personnel to use equipment, such as scanners to scan items being checked-out for use or in for return, and then items, such as wands with integral antenna, to waive over a medical procedure area (e.g., over a patient, over surrounding patient support surfaces (like bedding, gurneys, tables, etc.), surrounding equipment, personnel, waste receptacles, etc.) to locate the unaccounted for item. This takes up valuable time and does not provide the medical personnel with any additional information that would be helpful in locating the unaccounted-for item or information confirming for the user that they are using the equipment correctly.

Often times, these systems are also limited to a particular item (e.g., a sponge instead of other items/instruments used) and/or only track a small portion of a medical procedure area (e.g., around the sponge scanning system itself, etc.). For example, some smart sponge systems consist of a cart that includes a waste receptacle or bucket and track the sponges as used in the procedure. Such systems limit their product tracking to sponges alone and ignore the numerous other items/instruments utilized during a procedure (e.g., scalpels, scissors, tongs, gauze, mesh, suture needles, etc.). They also only track what is checked out and what is returned to the receptacle and do not track the surrounding procedure area. As mentioned above, they provide an antenna wand to search the surrounding procedure area that is not being tracked, but that requires medical personnel to perform additional tasks and does not confirm for the personnel if they are using the equipment appropriately.

Some conventional systems go beyond tracking sponges and offer counting or reconciliation features as well, but these systems often require medical personnel to apply machine readable labels on all items that are to be tracked, which is again labor intensive and adds more work for medical personnel, rather than reduces the steps they have to perform so they can focus on the procedure at hand and do so efficiently to make the best use of what often is very expensive high-tech operating room time. These systems often include interrogators that communicate with a base command unit to track a location of an object that has been marked with a machine-readable label so that the item can be tracked, but often this involves having the user scan via a scanner each item when checked out and then returned and then use a mobile wand antenna to scan for missing items. Less intelligent versions of such systems are also employed that simply use metal detection technology to detect if any item has been left behind in sensitive areas, however, conventional procedural arenas (e.g., clinics, operating rooms, etc.) are so inundated with metal objects, it is hard to use metal detection technology effectively and/or conveniently for such purposes.

Even in instances where medical kits are provided with pre-marked or pre-labeled items so that they can be tracked easier, these systems limit the tracking to those items in the kit and not additional items that may need to be employed during a procedure. In such systems, the focus is again on tracking a limited number of items and the procedural area, and again, the system operates blind either simply notifying personnel of a missing item or requiring personnel to scan surrounding area to locate the missing item. No further information is provided to the user to ensure they are properly performing their intended task.

Another problem associated with conventional systems is that they often rely too heavily on computer readable indicia that can only be detected by the electronic equipment used by the medical personnel. This precludes the medical personnel from being able to do their own secondary check for redundancy purposes and can leave medical personnel feeling concerned after a procedure is concluded because they do not have their own way to independently verify or confirm instrument tracking was complete.

Accordingly, it has been determined that a need exists for systems, methods and apparatus for improving medical procedures and medical procedure management, and, more particularly, to systems, methods and apparatus for tracking medical instruments throughout a procedure and assisting medical personnel throughout the procedure or at least at the conclusion of the procedure.

BRIEF DESCRIPTION OF THE FIGURES

Embodiments of the invention are illustrated in the figures of the accompanying drawings in which.

Figure 1:
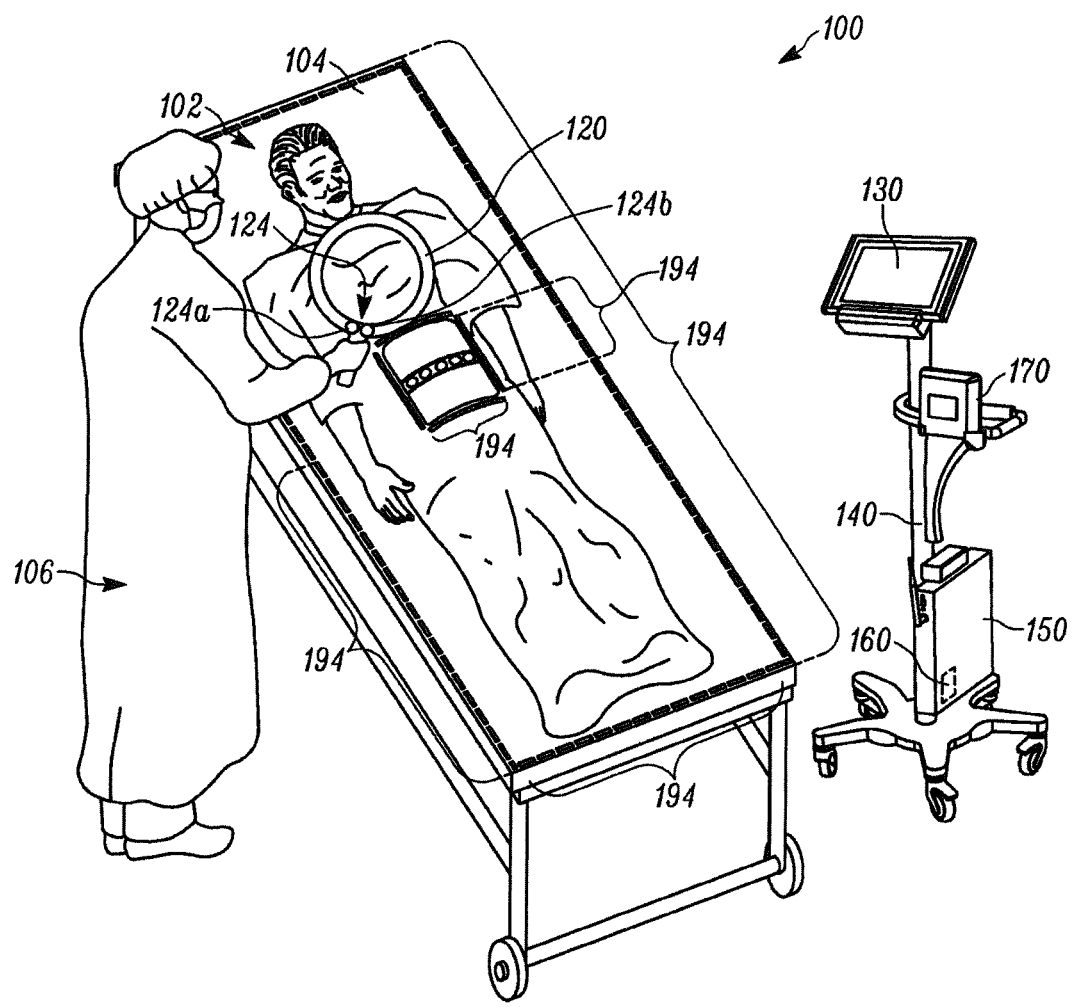
FIG. 1 is a perspective view of a medical procedural area/arena illustrating use of a wand with proximity sensors for ensuring the wand is used within a proper scanning range so that no retained objects may be left behind due to improper wand usage.

Elements in the figures are illustrated for simplicity and clarity and have not necessarily been drawn to scale or to include all features, options or attachments. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. Similarly, while distinct embodiments are discussed it should be understood that features from one embodiment may be combined with features of other embodiments in order to develop yet further embodiments and such further embodiments are contemplated herein. The terms and expressions used herein have the ordinary technical meaning as is accorded to such terms and expressions by persons skilled in the technical field as set forth above except where different specific meanings have otherwise been set forth herein.

DESCRIPTION OF THE INVENTION

Many variations of system or apparatus for improving medical procedures and medical procedure management are illustrated herein. In some embodiments, a wand is provided with sensors to indicate if the wand is capable of properly scanning a target area and/or if the wand is not capable of properly scanning the target area. In one form, the wand is provided with proximity sensors to ensure the wand is within a desired range of a patient prior to being used to check for retained objects relating to a medical procedure performed on the patient to reduce the risk retained objects will be missed or overlooked. In other forms, the wand is provided with motion sensors to ensure the wand is not moving too fast or in an improper orientation to scan the patient properly. In still other forms, the wand may include both proximity sensors and motion sensors to achieve both of the above-mentioned feats. In yet other embodiments, the wand is a wireless wand and the system may include further components such as a system interface (e.g., a wireless tablet), a network interface for providing an autonomous dedicated wireless network for the system components to communicate over, a scanner for scanning items or their packaging to help inventory, count or reconcile the items during or after the conclusion of a procedure, a receptacle for discarded items and/or a mobile cart for storing one or more of these system components. In still other embodiments, a camera may also be used to provide a medical procedure monitoring systems capable of monitoring an entire medical procedure room or area and tracking all items used therein. Related methods are also disclosed regarding such items and their use (e.g., utilizing such proximity sensors to ensure proper scanning of the items either throughout the procedure or at a conclusion thereof).

Figure 2:
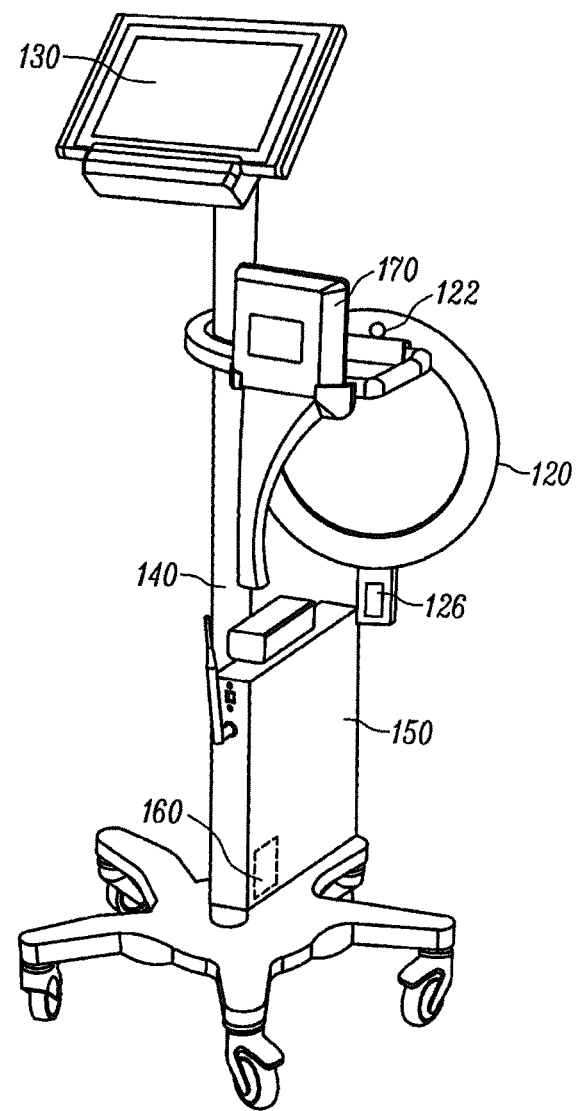
FIG. 2 is a perspective view of the wand system of FIG. 1 illustrating optional components for same in greater detail.

Turning now to FIGS. 1 and 2, there is illustrated a medical procedure area or arena 100 with a patient 102 resting on a patient support, such as operating table 104, a medical person or user of the system 106 and a wand 120 that includes a proximity sensor 122 (see FIG. 2). In the form shown, the wand 120 further includes an indicator 124 (see FIG. 1) and a controller 126 (see FIG. 2) that is in electronic communication and/or electrical connection with the proximity sensor 122 and indicator 124 and uses the indicator 124 to notify the user 106 when the wand 120 is either within a desired scanning range of a target area to be scanned or not within the proper scanning range (or both if so desired and configured).

The proximity sensor 122 may be any type of conventional proximity sensor capable of identifying when the wand 120 is within the desired scanning range of a target area. For example, the proximity sensor may be one or more of an optical proximity sensor, an ultrasonic proximity sensor, a sonar proximity sensor, a radar proximity sensor, a capacitive proximity sensor, an inductive proximity sensor, a doppler proximity sensor, a magnetic proximity sensor (e.g., a Hall effect proximity sensor, etc.). In some forms, the proximity sensor may include one or more components located only on the wand 120. While in other forms a more complex proximity sensor may be used including at least one component located on wand 120 and at least a second component located on or proximate the target area to be scanned (e.g., the patient drapes or covers may include or be lined with an item serving as the second component that interacts with the first component to provide proximity data).

Retained object systems or retained surgical items systems are known in the industry and include a variety of different wand configurations for detecting retained objects or, more particularly, the RFID tags on the medical instruments or objects used during the procedure. See, for example, the following U.S. patents issued to Haldor Advanced Technologies Ltd. including: U.S. Pat. No. 8,193,938B2 issued Jun. 5, 2012 and entitled "Apparatus for Identifying and Tracking Multiple Tools and Disposables", U.S. Pat. No. 8,872,662B2 issued Oct. 28, 2014 and entitled "Antenna, Apparatus and Method for Identifying and Tracking Multiple Items", U.S. Pat. No. 8,978,229B2 issued Mar. 17, 2015 and entitled "Device and Method for Attaching a Tag to a Tool" and U.S. Ser. No. 10/002,269B2 issued Jun. 19, 2018 and entitled "Mobile Handheld Antenna for Reading Tags", all of which are incorporated herein by reference in their entirety. In general, these wand systems include an antenna in the wand that detects tags placed on items used during the procedure so that the items may be found prior to the conclusion of the procedure and not left behind (particularly not left in the patient, such as in a patient cavity). The tags may be active (meaning they contain their own power source to transmit a signal) or passive (meaning they use the power emitted by the wand antenna to energize and transmit a signal), however, in most cases passive RFID tags are used due to the disposable nature of many of the items used in medical procedures. The signals received from the tags are transferred to a multiplexer which multiplexes the signals and transfers them to a reader to identify the unique identifier associated with each tag which the controller uses to determine what instrument (e.g., sponge, gauze, scalpel, scissors, clamp, etc.) has been detected by that unique identifier. In conventional systems the proper scanning range is typically within twenty inches (i.e., between 0"-20"), which is referred to as the "read range" of the wand. Some even have a smaller read range of between zero and sixteen inches (0"-16") or even zero and fourteen inches (0"-14"). These systems, however, fail to include features that allow a user to confirm if the wand 120 is within the desired scanning range of the target area to be scanned (e.g., within the read range of the wand) and thus can result in a user missing a retained object if the user 106 is not holding the wand 120 within the proper scanning range of the target area or read range. Given the speed at which medical staff are asked to work during procedures, it is feasible that personnel using a wand can inadvertently let the wand travel outside of the intended read range while scanning an area and/or patient which can ultimately lead to missed retained objects because the wand was too far away to pick-up the RFID tag.

In the wand system disclosed herein, the wand 120 includes any one of the above-mentioned proximity sensors as proximity sensor 122 and further includes an indicator 124 for alerting the user 106 when the wand 120 is either within the proper scanning range of the target area or outside of the proper scanning range (or both, if desired and so configured). In some instances, it may also be desired to provide notice once the read range threshold has been reached (and in some cases only providing notice of this threshold).

In the form shown, the indicator 124 may be at least one of a visual device, an audible device and/or a haptic feedback device, or any combination of these. In one form, the indicator 124 will be a visual device including at least one display. More particularly, in a preferred form, the display will comprise one or more lights, such as light emitting diodes (LEDs), or one multi-colored light, such as a multi-colored LED. In the form shown in FIG. 2, the indicator 124 is a display comprising a first LED 124a and a second LED 124b. The first LED 124a is a green LED and the second LED 124b is a red LED. When the wand 120 is outside of the desired scanning range from the target area to be scanned, the second/red LED 124b is illuminated to indicate to the user 106 that the wand is not within the proper scanning region. When the wand 120 is within the desired scanning range, the first/green LED 124a is illuminated to signify that the wand is within the proper scanning range. In a preferred form, the proximity sensor 122 is located on a first side of the wand 120 intended to be held face down by user 106 (or facing the target area to be scanned) and the indicator 124 is located on a second or opposite side of the wand intended to be visible to the user 106 as the proximity sensor 122 is held face down during scanning. In this way the user 106 can see the display 124 (e.g., LEDs 124a, 124b) while he or she is scanning the target area with the wand 120. In alternate forms, however, it should be understood that these items may be positioned on the same side of the wand 120 as each other (particularly in instances where the indicator 124 is not a visual indicator, but rather an audio device or haptic feedback device) or they may be faced on other sides of the wand that are not opposite one another such as adjacent sides, etc.

While two LEDs are shown (i.e., 124a, 124b), it should be understood that other forms of visual devices may be used. These alternate visual devices may be similar to LEDs, such as a multi-colored LED that can change from a first color (e.g., green) to a second color different than the first (e.g., red). Alternatively, a single light may be used (e.g., a green LED light solely to indicate when the wand is within read range, alternatively a red LED light solely to indicate when the wand is not within read range, etc.). In yet other alternate forms, different types of visual devices may be used entirely, such as a screen display (e.g., LED or LCD screen display, vacuum tube display, graphical user interfaces (GUIs) or touchscreens, needle-type analog meters, light bars, etc.). In addition, rather than just illuminating one light of color, the display 124 may illuminate multiple lights of the same or different colors to indicate proximity (e.g., illuminating a first light or first series of lights to indicate the wand 120 is not in proper scanning range and then a second or second series of lights to indicate the wand 120 is in proper scanning range). Multiple lights may also be used to indicate the proximity of the wand to the target area to be scanned. For example, in some forms, the display 124 may illuminate with one light (e.g., one green LED) once the read range threshold has been reached, and continue to illuminate similar colored lights as the wand moves closer to the target scan area to indicate the wand is closer (e.g., illuminating a second green LED when the wand gets to an intermediate position between the read range threshold and the target scan area, and a third green LED when the wand gets to a very close proximity of the target scan area (closer than the intermediate position). If more lights are desired, the range between the read range threshold and the target scan area can be broken up even further with lights representing each of those dissected areas. In still other forms, the light bar may illuminate a red light to indicate outside the read range and then others to indicate within the read range and signify the proximity to the target scan area.

As mentioned above, the indicator 124 may include an audio or audible device (this may be in addition to the display device or in lieu of the display device). Any conventional audible device may be used such as one or more of a speaker, buzzer, horn, etc., so that an audible alert can be provided when the wand 120 is within proper scanning range, when it is outside of proper scanning range, both (e.g., distinguishing the audible signal to distinguish whether the wand 120 is within proper scanning range or not), or simply when the read range threshold has been reached and that is it as discussed above with the visual display device. In a preferred form, the audible device indicator 124 will use a buzzer to make an audible alert or signal when the wand 120 is first brought within the read range of the target area (e.g., within twenty inches (20")) to alert the user 106 the wand is now within the appropriate scanning range so that the user 106 can start scanning and looking for retained objects. In other forms, the audible indicator 124 may be used to alert the user 106 if the wand leaves the proper scanning range, such as by issuing a sound signal from the buzzer once the wand leaves the read range. In a preferred form, the wand 120 may further include a mute input the user 106 can use to mute the audible indicator 124 so as not to annoy the user with the sound when the user intentionally has to move the wand outside of a specified area. In such forms, it is desired to keep the muting to a minimal amount of time to ensure the user 106 is properly notified if the wand 120 again leaves the proper scan range or read range, but in some forms the system may be configured to allow for predetermined periods of muting (e.g., 5 seconds, 10 seconds, 30 seconds, etc.) or may even allow the user to turn off the audible alert entirely if desired. In some forms, this input may actually be an "interrupt" input that allows users to turn on/off the various types of scanning features discussed herein. For example, a user with administrator-level permission, may be able to interrupt the indicators and notifications of the system, including interrupting the normal workflow of the system, not just temporarily muting sound. This may be desirable in situations where training with the wand is being performed and, thus, the user does not want the data collected to be combined with the data that is collected during actual procedures so as not to distort the actual procedural data collected to-date.

In alternate forms or in forms where the indicator 124 includes more than one form of indicator, the indicator 124 may include at least one haptic feedback device. In one form, the at least one haptic device is an actuator that vibrates when the wand 120 is either outside of the proper scanning range or within the proper scanning range. In a preferred form, the actuator is at lease one of a vibratory motor or a linear resonant actuator that causes the wand to vibrate when the wand is outside of the desired scanning range or read range. Thus, as user 106 is using the wand 120, they will receive some form of haptic feedback, such as vibration, if they raise the wand 120 above the desired scanning range (e.g., above twenty inches (20")). In other forms, the haptic feedback may be used to signify when the read range threshold has been reached.

As mentioned above, in alternate forms, any combination of the above-mentioned indicators may be used as indicator 124. For example, in a preferred form, the wand 120 will be equipped with all three indicators (e.g., visual, audible and haptic) and the audible device will emit an audio signal or alert when the wand 120 is brought within the read range of the target area to be scanned (just at the read range threshold) and will illuminate the visual device, such as green LED 124a, to signify to the user 106 that the wand 120 is within the proper read range. Once the user removes the wand 120 from the proper read range, the red LED 124b will illuminate and the haptic feedback device will continue to vibrate the wand 120 until the user 106 returns the wand 120 back to within the proper wand read range or returns the wand 120 to a storage location. In this way, the user is provided multiple different indications as to whether the wand 120 is within the proper scanning range while the user 106 is passing the wand over the medical procedure area 100. In a preferred form, this redundancy is used in order to ensure the user knows when the wand is within the proper read range and when he/she is outside the proper read range to ensure scanning with the wand is done only within the proper read range.

In the form shown in FIGS. 1 and 2, the wand 120 further includes a controller, such as integrated circuit or processor 126, which is electrically connected to the proximity sensor 122 and indicator 124 (either directly or indirectly) and controls operation of the indicator 124 based on the input provided from proximity sensor 122. In a preferred form, the controller 126 will be positioned on the same printed circuit board containing the wand antenna and the indicators present for that particular wand (e.g., visual indicator device, audible indicator device and/or haptic indicator device). In this way, the wand could be sold as its own stand-alone product if desired. In alternate forms, however, the wand 120 may be sold as a module system that can include numerous other modules or components or be provided at different product tiers (e.g., good/entry level with less options, better/mid-level with slightly more options, best/high-level with all options, etc.). For example, in the form shown in FIGS. 1 and 2, the wand system may further include a system interface, such as touch screen display 130. In a preferred form the wand 120 will be wireless and the touch screen 130 will be a wireless tablet that can be mounted to a mobile cart 140 for storage but removed as desired by user 106 or other users. In this way, the user 106 may carry the interface 130 with them if desired as they use the wand 120 (e.g., such as in situations where the proximity information or display 124 is provided on the interface 130 only and not on the wand 120 itself).

In some forms, the wand system may also include its own network connection 150 in order to ensure a highly efficient and private or dedicated local area network that the wireless wand 120 and wireless tablet interface 130 communicate over. This wireless connection 150 generates an autonomous dedicated wireless network (e.g., Wi-Fi network) for the system that the system components may use to ensure efficient wireless communication between all components (e.g., sufficient bandwidth, sufficient connection signal, etc.). If desired, the dedicated network could be opened up to other wireless components used in the procedural arena, however, in a preferred form this would require the entry of a password in order to keep the wireless connection 150 secured and protected from unwanted or unauthorized devices from being able to join the network.

Additional components that may be included with the wand system is a memory 160. In the form illustrated in FIGS. 1 and 2, the memory is shown for exemplary purposes as contained within the same structure as wireless network 150, however, it should be understood that memory 160 could be a local memory located elsewhere in the system, such as in interface device 130 or elsewhere in its own housing, or alternatively it could be located remotely from the wand system depicted via a network connected memory (not shown). For example, the memory 160 may be a cloud-based memory located at a cloud storage facility remote from the remainder of the wand system illustrated in the figures and accessible via a wide area network, such as the Internet.

Another additional component that may be included with the wand system is a scanner 170 for scanning instruments or their packaging to check them out prior to the procedure and/or check them in or reconcile them by confirming they are not still unaccounted for once the procedure is done to alert the users that an item is missing if in fact that is the case. In a preferred form, the scanner 170 will be able to read machine detectable or readable markers, such as bar codes, RFID sensors, alpha sequential markings, numeric sequential markings, alpha-numeric sequential markings, or just comprise a machine detectable image or shape. For example, in some forms, the instrument marker includes a bar code identifying the instrument and/or containing information about the instrument, such as a UPC, EAN, GTIN or other trade identification for identifying an item. For example, the scanner 170 may scan linear, two- or three-dimensional (2D, 3D) hydrophobic markings and be used by the user to scan in the items that will be used for the procedure so that those same items have to be rescanned in later once used in order to do an audit or reconciliation of the items used. If one is not scanned back in, then the user will take the wand 120 and search for the missing instrument. In the form shown, the scanner 170 includes a head with an elongated handle extended therefrom. The scanner 170 includes a scanner (such as an optical laser reader) on one side that and has its own display on the other opposite side to indicate what item was scanned. In one form, the scanner can stay mounted on the cart 140 and simply have the items held up in front of the optical side of the scanner to register them with the scanner. While in other forms, the scanner 170 can be removed from the cart 140 and handheld to hold the optical side of the scanner face down over the item to be scanned to scan same and indicate on the display located on the side facing upward opposite the optical scanner side what item has been scanned.

Figure 3:
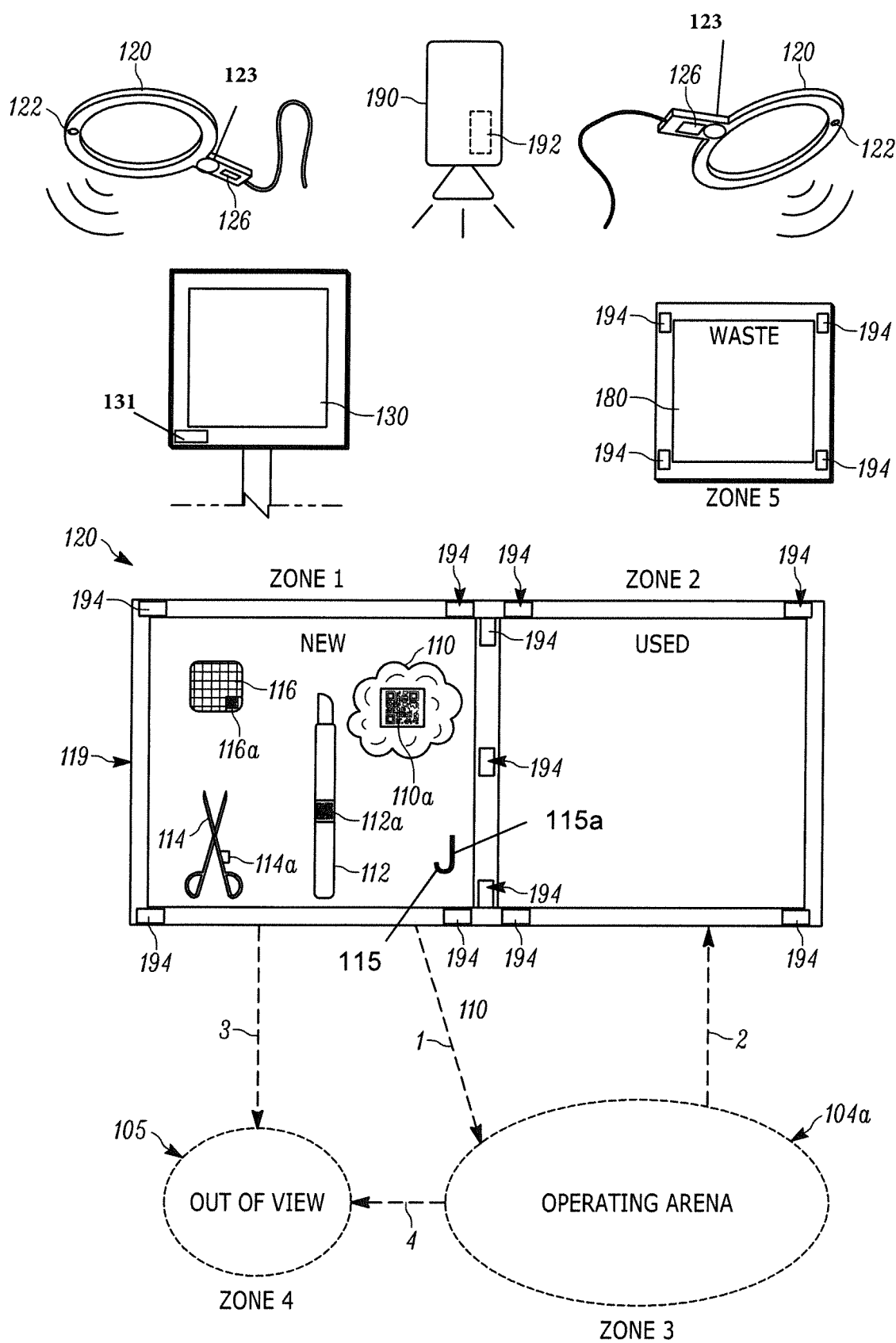
FIG. 3 is a schematic illustration of the wand system of FIGS. 1 and 2 further illustrating an optional camera for continuously monitoring instruments as they are used throughout the procedure.

In FIG. 3, the wand system is illustrated with the above features, but also having one or more motion sensors, such as accelerometers 123, which is used to detect the speed and/or orientation with which the wand is being moved to detect and warn if the user is moving the wand too fast or holding it in an improper orientation in order to properly scan the target area (e.g., patient, surrounding area, receptacles, etc.). While the illustrated system shows two wands 120, it should be understood that in some forms only one wand 120 will be provided with the system. The accelerometers 123 may be of the two-axis or three-axis type to detect two-dimensional (2D) or three-dimensional (3D) movement of the wand, respectively. In a preferred form, the accelerometers 123 will be three-axis, 3D accelerometers so that 3D movement of the wand 120 can be detected and monitored.

With the data the accelerometers 123 provide, the system 106 can determine if the wand 120 is moving too fast to properly scan the target area or if it is oriented in a way that is not appropriate or preferred for scanning the target area (e.g., held at too angled or tilted of a position). In one form, the system 106 is setup to accept zero to six seconds (0 s-6 s) per pass as an acceptable speed with which to wand the target area. In another form, however, the system 106 will be setup to accept zero to three seconds (0 s-3 s) per pass as an acceptable speed and will alert the user if the wand 120 is being moved faster than that speed. If desired, the range can be set to an even lower tolerance (e.g., 0 s-2 s) per pass. In a preferred form, the wand system will be configured such that the target speed threshold of the wand can be adjusted to allow customization for different intended uses or workflows (e.g., allowing the user to set one speed for a torso procedure, another speed for a knee procedure, etc.). In still other forms, the system will allow customization to account for the size of the patient being scanned as well. For example, in a preferred form, the system will be configured with a distance buffer that is used to ensure proper scan penetration. Thus, for more petite patients, the wand may be held at a further distance from the patient and still have enough penetration to satisfy the distance buffer set for the wand. However, in other instances where a much larger patient is being scanned, the system may be set to require the wand be held closer to the patient in order to ensure sufficient scan penetration to satisfy the distance buffer requirements of the system.

In a preferred form, the wand scan will take 30-40 seconds (30 s-40 s), however, in alternate arrangements it may be twenty to 60 seconds (20 s-60 s). A reason for the speed control and/or orientation positioning control is to ensure that the wand is not in an undesirable state for detecting any items from a procedure to minimize the risk that an item could be left behind. As for orientation, it is desirable to keep the wand 120 perpendicular to the target area being scanned. In one form, a zero to thirty degrees) (0°-30° tolerance may be maintained. In other forms, the tolerance may be tighter, such as zero to twenty degrees) (0°-20° from perpendicular. In still other forms, the motion sensor may also include a gyroscope to assist with detecting rotational movement of the wand or, more likely, a combination of both accelerometer and gyroscope. For example, in procedures involving implants such as a knee transplant, it may be desirable to also detect the rotational movement of the wand to ensure the user has appropriately wanded around the entire knee completely before confirming the procedure can conclude.

Numerous different types of motion sensors may be used for wand 120 so long as they convey the desired wand parameters to determine if the wand 120 is sufficiently positioned to scan the target area. For example, any one of the following motion sensing controllers may be used, including: U.S. Patent Application Publication No. 20150261291A1, published Sep. 17, 2015, entitled "Methods and systems tracking head mounted display (HMD) and calibrations for HMD headband adjustments"; U.S. Patent Application Publication No. 20060256081A1, published Nov. 16, 2006, entitled "Scheme for detecting and tracking user manipulation of a game controller body"; U.S. Patent Application Publication No. 20060287086A1, published Dec. 21, 2006, entitled "Scheme for translating movements of a hand-held controller into inputs for a system"; U.S. Patent Application Publication No. 20060264260A1, published Nov. 23, 2006, entitled "Detectable and trackable hand-held controller"; U.S. Patent Application Publication No. 20060287087, published Dec. 21, 2006, entitled "Method for mapping movements of a hand-held controller to game commands"; U.S. Patent Application Publication No. 20070015559A1, published Jan. 18, 2007, entitled "Method and apparatus for use in determining lack of user activity in relation to a system"; U.S. Patent Application Publication No. 20070015558A1, published Jan. 18, 2007, entitled "Method and apparatus for use in determining an activity level of a user in relation to a system"; U.S. Patent Application Publication No. 20060282873A1, published Dec. 14, 2006, entitled "Hand-held controller having detectable elements for tracking purposes"; U.S. Patent Application Publication No. 20080100825A1, published May 1, 2008, entitled "Mapping movements of a hand-held controller to the two-dimensional image plane of a display screen"; U.S. Patent Application Publication No. 20080098448A1, published Apr. 24, 2008, entitled "Controller configured to track user's level of anxiety and other mental and physical attributes"; and U.S. Patent Application Publication No. 20080096654A1, published Apr. 24, 2008, entitled "Game control using three-dimensional motions of controller" the entire disclosures of which are all incorporated herein by reference in their entirety.

Figure 5:
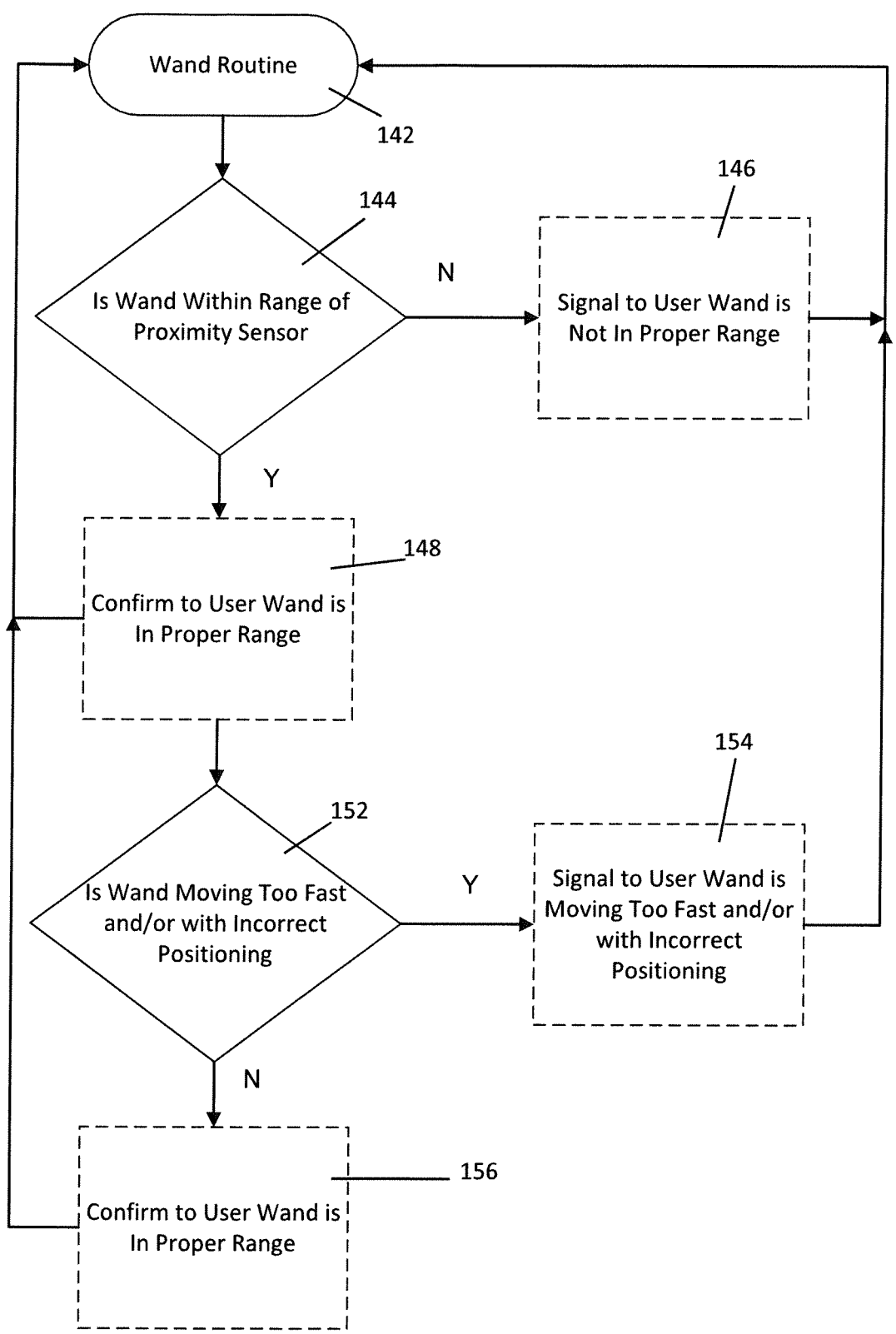
FIG. 5 is a flow chart illustrating another exemplary software routine operated by the wand system to notify the user when the wand is moving too fast for proper scanning and/or in an incorrect position or alignment that is not desired for proper scanning.

In some forms, the system may be provided with a single sensor (e.g., a proximity sensor or a motion sensor), however, in a preferred form, the system will include both a proximity sensor and a motion sensor in order to assist the user in confirming when the system is used in the appropriate way (as will be discussed with FIG. 5 below). It should be understood, however, that features of one embodiment discussed herein may be combined with features of other embodiments herein to create numerous other embodiments, and all are contemplated to be covered by the disclosure herein.

As will be discussed further with respect to FIG. 3, the wand system may further include a receptacle 180 for receiving discarded items and/or a camera 190 for monitoring the procedural area to track instruments as they are being used and provide the user with more information about the procedure (e.g., how instruments were used, where, when, etc.) and about missing items (e.g., where was the item last seen by the camera, what direction was it traveling, where does the system believe it has gone, etc.). Thus, the wand system could be setup to continually track instruments throughout the procedure to provide more than just a post procedure reconciliation of used items (e.g., a conventional wand system used to check for retained objects). For example, in the form illustrated in FIG. 3, the system or apparatus may include camera 190 positioned for viewing a procedural area (e.g., whether that be limited to a prep table, a larger portion of the procedural area beyond just the prep table, the entire room, etc.) so that the system or apparatus can track movement and/or detect positioning of a plurality of medical instruments during a medical procedure as at least one of the plurality of medical instruments is moved between multiple zones of the procedural area at least including a first prep zone and a second procedure zone. The camera 190 may include its own controller 192 or interface 130 may control the operation of camera 190. In yet other forms, item 192 may comprise on-camera memory storage for storing images or video, if desired. In a preferred form, the camera will interface with system interface 130 similar to how the scanner 170 and wand 120 interface with system interface 130. A variety of different types of cameras may be employed for camera 190, however, in a preferred form, the wand system or apparatus will only require one camera 190 for monitoring the desired procedural area, rather than requiring two or more cameras for monitoring specific portions of the procedural area (e.g., one camera for the prep table, another camera for the patient area, another camera for the waste receptacle(s), etc.).

The camera 190 will be connected to the system or apparatus via either direct connection via cable or wireless connection (e.g., RF transceiver setup, Wi-Fi, NFC, Bluetooth/BLE, etc.) or via a network interface which may also be wired (e.g., Ethernet, USB, etc.) or wireless (RF, Wi-Fi, NFC, Bluetooth/BLE, etc.). In a preferred form, the camera 190 will interface with controller 130 via the dedicated Wi-Fi network interface 150 discussed above. The camera 190 may be connected in the procedural area in numerous different ways (e.g., connected to the ceiling, light fixtures, other existing medical equipment carts or towers, a prep table, etc.), however, in a preferred form, the camera may be mounted to the mobile cart 140 and extended high above same via a boom or support beam extending from the cart 140 so that it is brought into the procedural area by the medical personnel and not left there permanently.

In FIG. 3, the procedural area is separated into separate zones so that the camera and system can identify a specific zone that any given instrument has been used during the procedure to track the instruments and give and/or store additional information or data relating to the procedure. In the form shown, markers, such as zone markers 194, are used to separate the procedural arena into: Zone 1—starting tray area where instruments are initially located; Zone 2—the used instrument area; Zone 3—the operating arena as delineated by zone markers 104a (see FIGS. 1 and 3); Zone 4—out of camera view; and Zone 5—discard/waste receptacle. Instruments such as a sponge 110, scalpel 112, scissors 114, needle 115 and gauze 116 are shown in the initial setup area of Zone 1 and marked with respective RFID tags 110a, 112a, 114a, 115a and 116a, respectively. With this configuration, the camera 190 can be used to track the instruments 110-116 as they are moved from the prep area of Zone 1, to the operating or procedural area 104a and back to the used/discard area of Zone 2 or receptacle 180 of Zone 5. If the instruments go missing at any time, such as out of camera view Zone 4 (which in this form is the default for any item not found within one of the other zones), the system will alert the user in the manner set forth in U.S. Pat. No. 10,154,885B1 issued to Medline Industries on Dec. 18, 2018 and entitled "System, apparatus and methods for continuously tracking medical items throughout a procedure" which is incorporated herein by reference in its entirety. As mentioned in this incorporated patent, the markers may denote other items beyond zones as desired or configured by the user.

Thus, it should be understood that disclosed herein is an apparatus for improving medical procedures that includes a wand system having a wand 120 with proximity sensors 122, an indicator 124 for identifying if the wand 120 is within the wand read range and a control circuit 126 with a non-transitory computer readable memory storing a set of instructions executable by the control circuit 126 and configured to cause the control circuit 126 to perform the steps of: indicating via the indicator 124 when the wand 120 is within a proper scanning range (e.g., within proper read range) or outside of proper scanning range; and notifying the user when the wand 120 is outside of the proper scanning range so that the wand 120 can be moved closer to the target area for proper scanning.

Figure 4:
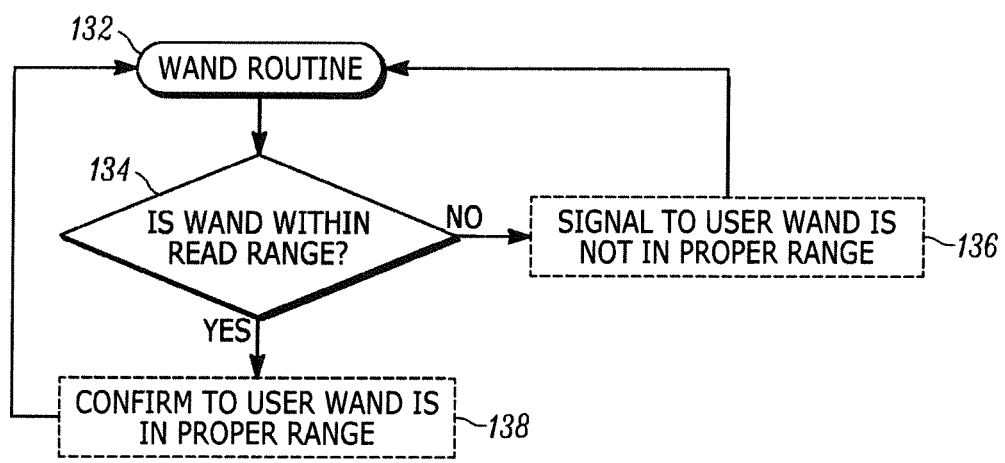
FIG. 4 is a flow chart illustrating an exemplary software routine operated by the wand to notify the user when the wand is within proper scanning range and/or when it is not within proper scanning range in order to ensure retained objects are not missed because of incorrect use of the wand.

A flow chart exemplifying this wand routine is illustrated in FIG. 4. The wand routine is initiated in step 132, and a determination is made in step 134 if the wand 120 is within read range or proper scanning range. It should be understood that the system can be setup in many different optional ways as discussed above. For example, in one form the system may be setup to only alert the user when the wand 120 is not within proper read range (e.g., visual indicator, audible indicator, haptic indicator, combination and one or more of these, etc.). Alternatively, it can be setup to only alert the user when the wand 120 is within proper read range (e.g., visual indicator, audible indicator, haptic indicator, combination and one or more of these, etc.). In a preferred form, however, the system will be setup to provide the user with feedback telling the user if the wand 120 is outside of proper read range and if the wand 120 is within proper read range so that the user can definitively tell at any given moment whether the wand 120 is inside of or outside of proper read range. For example, the system will make an audible alert when the wand 120 enters the read range threshold and illuminate a visual indicator (e.g., a steady light of a certain color, a flashing light of a certain color, etc.) to indicate same for as long as the wand 120 remains in the read range. Once the wand leaves the read range, the wand 120 will provide a haptic feedback via a haptic feedback device and illuminate a visual indicator (e.g., a steady light of a certain color, a flashing light of a certain color, etc.) indicating that the wand is no longer within proper read range for the entire time the wand is out of range until the wand 120 is returned back to its mobile stand 140. In other forms, these notices or alerts may only be provided for a period of time (e.g., 5 seconds, 10 seconds, 30 seconds, 1 minute, etc.). For example, in one alternate form, the system will perform as discussed above with respect to the preferred form, however, the haptic feedback indicating the wand is not within proper read range will only last for 30 seconds and an audible sound will be made when the wand leaves proper read range to further alert the user of same. In other forms, the audible beep may be a continuous sound signal while the wand 120 is outside of read range and/or it may be an audible signal that lasts for a predetermined period of time (e.g., see time examples above) In some forms, the user will be able to configure these options for the wand 120 so that he/she can set it up as they would like it.

In some forms, the user interface 130 will preferably be used to control (e.g., program settings of, monitor, etc.) the wand 120, scanner 170 and network interface 150. The wand will preferably include an onboard controller 126 that controls indicator 124 based on data received from proximity sensor 122, however, in other forms this may be controlled via user interface 130. Regardless of whether there is an onboard controller 126 or a master controller 130, the system or apparatus will preferably be configured to improve medical procedures by including a wand system having a wand 120 with at least one proximity sensor 122, and indicator 124 and a control circuit 126 or 130 with a non-transitory computer readable memory storing a set of instructions executable by the control circuit 126 or 130 and configured to cause the control circuit to perform the steps of: indicating via the indicator 124 when the wand 120 is within a proper read range or outside of a proper read range; and notifying the user when the wand 120 is outside of the proper read range so that the wand can be moved closer to a target area for proper scanning of the target area. In some forms, the indicator 124 includes a visual device and at least one of an audible device and/or a haptic feedback device and the non-transitory computer readable memory storing the set of instructions executable by the control circuit 126 or 130 is further configured to indicate via the visual device when the wand is within the proper read range for wand scanning and to indicate via the at least one of the audible device and/or haptic feedback device when the wand is outside of the proper read range for wand scanning. In still other preferred forms, the indicator 124 includes the visual device, the audible device and the haptic feedback device and the non-transitory computer readable memory storing the set of instructions executable by the control circuit 126 or 130 is further configured to indicate via the visual device and the audible device when the wand is within the proper scanning range and to indicate via the audible device and the haptic feedback device when the wand is outside of the proper scanning range.

In alternate forms, where both proximity sensors 122 and motion sensors 123 are used, the process may involve not only tracking the proximity of the wand to the target area, but also the speed and/or orientation relating to the wand to determine if the system is appropriately setup and being used to scan the target area properly. For example, the controller 126 may be connected to the proximity sensors 122 and motion sensors 123 and programmed to run an alternate software routine as illustrated in FIG. 5. In this exemplary wand routine 142, the wand 120 checks to see if the wand 120 is in the range of the proximity sensor 122 in step 144. If not, the system may be configured to signal the user that the wand 120 is not in the proper read range as illustrated in step 146. If the wand is within proper read range, the system may then confirm to the user that the wand 120 is within the proper read range in step 148. Given the addition of the motion sensor 123, the wand 120 can also determine if the wand 120 is being moved too fast and/or in an undesirable orientation for properly scanning the target area in step 152. If the wand 120 is being moved too fast or in an improper orientation, the wand 120 will alert the user in step 154 using any one of the indication methods discussed above or any combination thereof (e.g., visual display/light, sound, haptic feedback, etc.). If the wand 120 is being moved at a proper speed and orientation the wand 120 can optionally confirm this to the user in step 156 using any one of the indication methods discussed above or any combination thereof. In a preferred form, the wand 120 will be setup to consider being within sixteen inches (16") of the target area to be scanned as being within the proper read range, traveling at a speed equal to or less than three seconds (<3 sec.) to be a proper scan speed and being perpendicular or ninety degrees to the target area for scanning plus or minus thirty degrees (90°±30°) to be a proper wand orientation. These parameters are merely exemplary and may be altered depending on system setup and/or intended use.

With some system configurations, it may be desirable to provide confirmation of proper usage via the indicators as well as notifying of improper usage. In other configurations, it may be desirable to provide just one of those (i.e., just using the indicators to confirm proper usage or just using the indicators to notify of improper usage). All of these various configurations are intended to be covered by this disclosure. Similarly, while preferred embodiments are discussed herein as to which indicators will be used when (e.g., lighting an LED green when the wand is close enough to the target area or within read range and traveling at a proper speed and orientation to the target area, using a brief audible alert to signify when the wand moves into proper read range, and lighting an LED red and providing haptic and audible alerts when the wand is out of proper read range, is traveling too fast or in an improper orientation), it should be understood that numerous different combinations of these may be used for such purposes and all of these combinations are intended to be covered by this disclosure. For example, it may be desirable to break the use of the haptic feedback and audible alerts up so that one indicates one thing and the other another (e.g., using the audible alert to indicate the wand is out of proper read range and using the haptic feedback to indicate the wand is traveling too fast or in an improper orientation).

In addition to the above, disclosed herein is a system and method that collects data from the above identified examples. In some forms, this information will be tracked and used to identify what procedures were done well and what procedures could have been done better (e.g., a catalog or database of scanning science to be used and learned from over time). In a preferred form, the data will be used and stored in a database of all such procedures for use in later data mining to help determine best practices and/or practices to avoid (e.g., what scan pattern worked best for a particular procedure, what average scan speed (or pace) did successful procedures follow, what average distance (or proximity) was the wand held at during successful procedures, what wand type has the best results for a particular procedure, was a full body scan conducted or a partial body scan, was a room scan conducted, was a room scan conducted before or after a body scan, what common element existed in procedures that did not go well). In some configurations, the system will provide real-time reporting or feedback to the user indicating the quality of the wanding method being used by the user. The system may also prevent personnel from closing a case or procedure out until proper wand technique is achieved. In preferred forms, the system will work with other medical equipment to prevent such a close out until a proper body scan of the patient and proper room scan was done after the body scan.

As should be evident by the above examples, numerous types of data can be collected with the wand system and this data can equally be used in numerous different ways (some right away such as the real-time feedback example given above, others much later down the road such as the research and education examples given above). As medical equipment makers learn of this available data and its uses, it is contemplated that more and more medical devices will be configured to interface with one another to share this data and utilize it to ensure that all proper steps are taken before a procedure is concluded (or before it can be closed out). In this way, the data may be used to help control workflow for the procedure (e.g., procedural process steps, reporting, notifications, interfaces, etc.) to help improve overall medical procedures. For example, in some configurations this data will recognize problems as they happen and require counteractions to make-up for same, such as requiring the user to restart the entire scanning process if it is detected that the wand was used improperly during the prior scan. This may mean that this is done the moment a single improper usage is detected (e.g., out of scan read range, moving too fast, held in the wrong orientation, etc.), or the system may be configured to do this after a certain number of improper usages are detected. In a preferred form, the number of improper usage detections and types of improper usage will all be part of the data studied over time to perfect exactly what should cause the user to restart the entire scan (e.g., for example, it may be found in conventional knee replacement procedure that being out of read range up to three times is acceptable, but moving over the desired scan speed just once is enough to merit restarting of the entire scan).

The system may also be setup to require the user to provide biometric input or interface before using the wand to utilize this information along with the wand information. For example, the system may be equipped with a fingerprint scanner 131 (FIG. 3) that a user will have to use before operating the system and the system will store that biometric information along with the data collected from the use of the wand for later review and/or use. In this way, a party using the wand can be tracked down to confirm who used the device during any portion of the proceeding. This information could also be used to confirm who used the wand, how many people used the wand during a procedure, etc. In a preferred form, the system will require use of the biometric input 131 to log into the system. While the system shows the biometric input 131 being located on display 130, it should be understood that in alternate configuration the biometric input 131 may be located on the wand 120, the scanner 170 or elsewhere on the system. In some forms, all components may have such a biometric input and require the input prior to the component being used.

In addition to the systems and apparatus discussed herein, it should be understood that numerous methods are also disclosed herein. For example, a method for confirming a scanning device is within a proper read range is disclosed herein. Other methods include methods of manufacturing and/or using a item retention wand are disclosed, as are methods of detecting wands within proper read range, methods for signaling object retention wand positions (e.g., within proper read range, outside of proper read range, at threshold of proper read range, etc.), methods of providing automatic visual, audible and/or haptic feedback to object retention wand users.

Thus, it should be understood that numerous methods, systems and apparatus are disclosed herein for improving medical procedures, confirming when a wand is within proper scanning range, and tracking medical instruments (or items) when desired. This detailed description refers to specific examples in the drawings and illustrations. These examples are described in sufficient detail to enable those skilled in the art to practice the inventive subject matter. These examples also serve to illustrate how the inventive subject matter can be applied to various purposes or embodiments. Other embodiments are included within the inventive subject matter, as logical, mechanical, electrical, and other changes can be made to the example embodiments described herein. Features of various embodiments described herein, however essential to the example embodiments in which they are incorporated, do not limit the inventive subject matter as a whole, and any reference to the invention, its elements, operation, and application are not limiting as a whole, but serve only to define these example embodiments.

This detailed description does not, therefore, limit embodiments of the invention, which are defined only by the appended claims. Each of the embodiments described herein are contemplated as falling within the inventive subject matter, which is set forth in the following claims. Further, it should be understood that features of one embodiment described herein may be combined with features of other embodiments described herein in order to develop yet further embodiments and such further embodiments are contemplated within this disclosure.

What is claimed is:

1. An object retention wand system comprising:
   a wand body having a handle for holding the wand;
   a sensor located on or in the wand body for use in determining when the wand is capable of properly scanning a target area;
   a first indicator that provides a first type of indication when it is determined that the wand is capable of properly scanning the target area; and
   a second indicator that provides a second type of indication different from the first type of indication when it is determined that the wand is not capable of properly scanning the target area.

2. The object retention wand system of claim 1 wherein the sensor is a proximity sensor and/or a motion sensor.

3. The object retention wand system of claim 2 wherein the sensor includes at least one proximity sensor and the proximity sensor includes one or more of an optical proximity sensor, ultrasonic proximity sensor, sonar proximity sensor, radar proximity sensor, capacitive proximity sensor, inductive proximity sensor, doppler proximity sensor and/or magnetic proximity sensor.

4. The object retention wand system of claim 1 wherein the first indicator and the second indicator are at least one of a visual device, an audible device and/or a haptic device.

5. The object retention wand system of claim 4 wherein the first and the second indicator are a visual device and the visual device is a display.

6. The object retention wand system of claim 5 wherein the display includes one or more LEDs.

7. The object retention wand system of claim 6 wherein the one or more LEDs includes a multi-colored LED capable of switching between a first color and a second color, and wherein the first type of indication includes the multi-colored LED being illuminated in the first color and wherein the second type of indication includes the multi-colored LED being illuminated in the second color.

8. The object retention wand system of claim 4 wherein the second indicator is an audible device comprising at least one of a speaker, buzzer and/or horn.

9. The object retention wand system of claim 8 wherein the second type of indication is an audio signal from the audio device.

10. The object retention wand system of claim 4 further comprising a user input for muting or interrupting the first or second indicator after it has initially provided a notification relating to the wand.

11. The object retention wand system of claim 1 wherein the second indicator includes a first LED which is illuminated in a first color when the sensor indicates that the wand is not capable of properly scanning the target area, and wherein the first indicator includes a second LED which is illuminated in a second color, different than the first color, when the sensor indicates the wand is capable of properly scanning the target area.

12. The object retention wand system of claim 1 further comprising a buzzer which provides an audio signal to indicate when the wand has transitioned from a first position where the wand is not capable of properly scanning the target area to a second position where the wand is capable of properly scanning the target area to alert the user of same and/or vice versa.

13. The object retention wand system of claim 1 further comprising a controller electrically connected to the sensor, and the first and second indicators for operating the first and second indicators according to data provided by the sensor.

14. The object retention wand system of claim 13 further including a user interface for communicating with the wand.

15. The object retention wand system of claim 14 wherein the user interface is a wireless tablet and the wand communicates wirelessly via the wireless tablet.

16. The object retention wand system of claim 15 further comprising a network interface for providing a dedicated local area network for the wireless wand and wireless tablet to connect to so as to ensure efficient wireless communication between the wand and the user interface.

17. The object retention wand system of claim 15 further including a scanner for scanning instruments prior to their use in a procedure or post their use in a procedure.

18. The object retention wand system of claim 17 wherein the scanner is a wireless scanner that is connected to the wireless tablet via the network interface.

19. The object retention wand system of claim 17 further including memory for storing data relating to the use of the wand and/or scanner, the memory being located either locally on the system or remotely accessible via the network interface.

20. The object retention wand system of claim 19 wherein the memory is located either locally on the system or remotely accessible via the network interface.

21. The object retention wand system of claim 17 further including a receptacle for receiving discarded items after use in a procedure.

22. The object retention wand system of claim 17 further comprising a mobile cart having a wheeled base and interfaces for mating with the wand, user interface, scanner and network interface to securely connect the wand, user interface, scanner and network interface to the mobile base so that they may be transported together as an assembly.

23. The object retention wand system of claim 22 wherein the interfaces are sockets or nests which the wand, user interface, scanner and network interface can securely connect to the mobile base.

24. The object retention wand system of claim 1 wherein the sensor is a motion sensor comprising an accelerometer for detecting two-dimensional or three-dimensional movements of the wand.

25. The object retention wand system of claim 1 further comprising an interrupt input that can be activated to disrupt a normal workflow of the system for at least a period of time.

26. The object retention wand system of claim 1 further comprising a biometric input or interface which a user is required to use in operation of the wand system so that user information can be tracked along with other system data.

27. An object retention wand system comprising:
a wand body having a handle for holding the wand;
a sensor located on or in the wand body for determining when the wand is capable of properly scanning a target area; and
at least one haptic feedback device that includes an actuator that vibrates when the wand is not capable of properly scanning the target area and/or when the wand is capable of properly scanning the target area.

28. The object retention wand system of claim 27 wherein the actuator is at least one of a vibratory motor or a linear resonant actuator that causes the wand to vibrate when the wand is not capable of properly scanning the target area.

29. An object retention wand system comprising:
a wand body having a handle for holding the wand;
a sensor located on or in the wand body for determining when the wand is capable of properly scanning a target area; and
at least one haptic feedback device that includes an actuator that vibrates when the wand has transitioned from a first position where the wand is not capable of properly scanning the target area to a second position where the wand is capable of properly scanning the target area to alert the user of same and/or vice versa.

30. An object retention wand system comprising:
a wand body having a handle for holding the wand;
a sensor located on or in the wand body for determining when the wand is capable of properly scanning a target area; and
an indicator that includes a visual device, an audible device and a haptic feedback device,
wherein the visual device provides a first visible indication when the wand is capable of properly scanning the target area and a second visible indication when the wand is not capable of properly scanning the target area, and
wherein the audible device provides an audio signal when the wand is not capable of properly scanning the target area and the haptic feedback device provides a haptic feedback when the wand is not capable of properly scanning the target area.

\* \* \* \* \*